United States Patent [19]

Schleppinghoff et al.

[11] Patent Number: 4,503,265
[45] Date of Patent: Mar. 5, 1985

[54] PROCESS FOR THE PRODUCTION OF METHYL TERT.-BUTYL ETHER (MTBE) AND OF HYDROCARBON RAFFINATES SUBSTANTIALLY FREED FROM I-BUTENE AND FROM METHANOL

[75] Inventors: Bernhard Schleppinghoff, Dormagen; Martin Becker, Cologne, both of Fed. Rep. of Germany

[73] Assignee: EC Erdolchemie GmbH, Koeln-Warringen, Fed. Rep. of Germany

[21] Appl. No.: 442,692

[22] Filed: Nov. 18, 1982

[30] Foreign Application Priority Data

Dec. 4, 1981 [DE] Fed. Rep. of Germany ....... 3148109

[51] Int. Cl.$^3$ ............................................. C07C 41/06
[52] U.S. Cl. .................................... 568/697; 568/699
[58] Field of Search ................................ 568/697, 699

[56] References Cited

U.S. PATENT DOCUMENTS 3,979,461  9/1976  Ancillotti et al. .................. 568/697
4,320,232  3/1982  Volkamer et al. .................. 568/697

FOREIGN PATENT DOCUMENTS 2802198  7/1979  Fed. Rep. of Germany.
2853769  6/1980  Fed. Rep. of Germany.
2908426  9/1980  Fed. Rep. of Germany.

Primary Examiner—Natalie Trousof
Assistant Examiner—Bruce D. Gray
Attorney, Agent, or Firm—Sprung, Horn, Kramer & Woods

[57] ABSTRACT

In the reaction of methanol and of i-butene which is contained in a hydrocarbon mixture on an acid cation exchange material to give methyl tert.-butyl ether (MTBE), methanol and i-butene can be used in essentially equimolar amounts if simultaneously to the distillative separation of the etherification mixture into its constituents this etherification mixture is passed into a secondary reaction. To do this, the etherification mixture is fed into a distillation column and from above the feed-in point a liquid distillate stream is taken off and passed in a secondary reactor over an acid cation exchange material. The mixture leaving the secondary reactor is returned below its take-off point.

9 Claims, 1 Drawing Figure

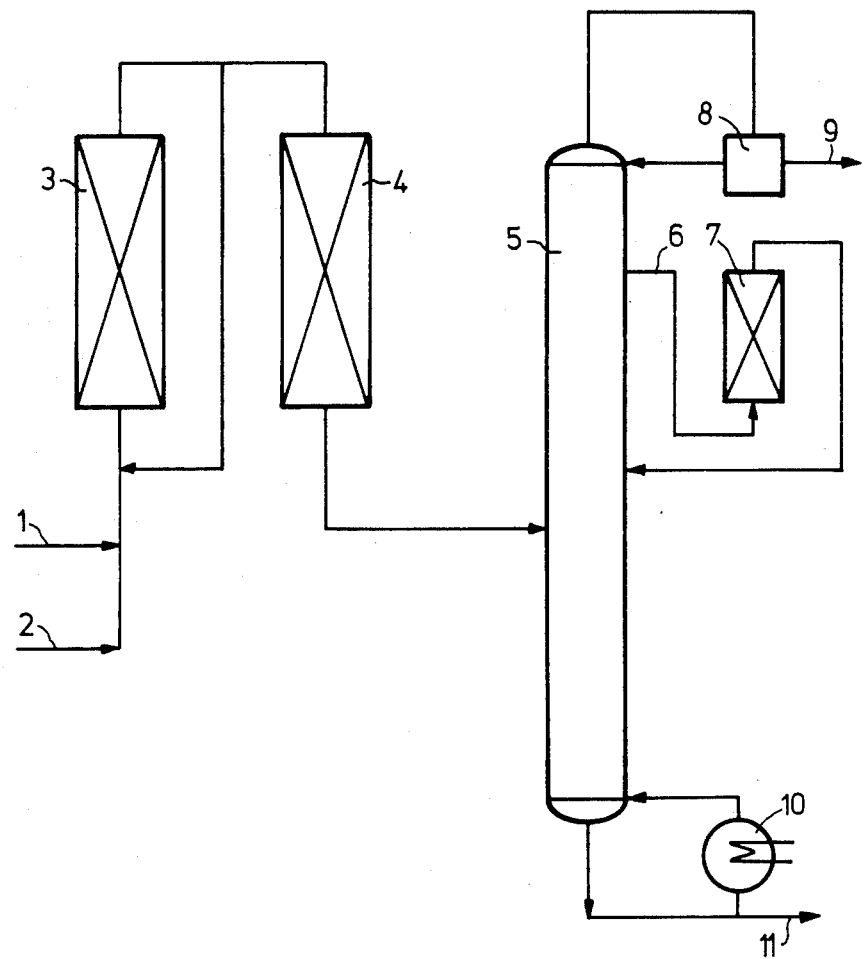

PROCESS FOR THE PRODUCTION OF METHYL TERT.-BUTYL ETHER (MTBE) AND OF HYDROCARBON RAFFINATES SUBSTANTIALLY FREED FROM I-BUTENE AND FROM METHANOL

The present invention relates to a process for the simultaneous production of methyl tert.-butyl ether (MTBE) and of hydrocarbon raffinates, both the former and the latter being substantially free of i-butene and of methanol.

MTBE serves, for example, as a carburettor fuel additive to improve the octane number and as a solvent and extracting agent which, in contrast to many other ethers, forms almost no peroxides. MTBE is also suitable as a starting material for the preparation of pure i-butene via the ether cleavage.

It is known to react i-butene and methanol on acid ion exchange materials to give MTBE (German Pat. No. 1,224,294). Since this reaction is very selective, suitable feed materials are in particular also mixtures of i-butene with other hydrocarbons, as obtained, for example, in thermal or catalytic crackers.

It is desirable to convert, as far as is possible, all the i-butene in such mixtures. For this purpose, a large excess of methanol is generally used (German Offenlegungsschrift No. 2,853,769). Another reason which makes it desirable that the conversion of i-butene present in the C$_4$-raffinates is as complete as possible is that to utilise further the i-butene-free C$_4$-raffinate the residual content of i-butene should be below 2% by weight, if possible even under 1 or under 0.5% by weight. This specification is necessary, for example when maleic anhydride, methyl ethyl ketone, butene-1 or octene (by dimerization) is intended to be produced from these residual mixtures which are usually referred to as C$_4$-raffinate II. From this point of view of the further processing, it must also be ensured that the C$_4$-raffinate II no longer contains any methanol. To obtain a raffinate which meets the specification, particular requirements must therefore be satisfied. However, it has become clear that, due to azeotropic effects, simple distillation cannot produce a methanol-free C$_4$-raffinate II (compare German Offenlegungsschrift No. 2,802,198, page 3, paragraph 3).

For reasons of further processing, transport and storage, the methanol content in MTBE should not exceed 3% by weight to 5% by weight. Since MTBE also forms an azeotrope with unconverted methanol, separation into the individual components is not possible by simple distillation. To remove the methanol from the C$_4$-raffinate II and from the MTBE/methanol azeotrope, a water wash has been proposed as a suitable method (German Offenlegungsschrift No. 2,246,004 and U.S. 3,726,942). However, the working-up of the resulting aqueous methanol and the drying of the remaining materials, namely MTBE and C$_4$-raffinate II, are undesirable additional steps which are expensive to operate and require large investments.

A further process variant to obtain high i-butene conversions is a two-stage etherification with an intermediate C$_4$-separation (German Offenlegungsschrift No. 2,521,964 and U.S. Pat. No. 3,979,461). The reaction product of the first stage is separated into its individual components in a distillation column. The top product, which still contains unconverted i-butene and methanol, is passed in a second stage into a secondary reaction. The reaction product of the second stage is separated into its components in a second distillation column. This process also requires a high outlay in energy and investment.

A process has now been found for the production of methyl tert.-butyl ether (MTBE) and of hydrocarbon raffinate which is substantially free of i-butene and of methanol from methanol and a hydrocarbon mixture containing i-butene, by etherification on acid cation exchange materials, which process is characterised in that methanol and the i-butene contained in the hydrocarbon mixture are used in essentially equimolar amounts and, simultaneously to the distillative separation of the etherification mixture into its constituents, a part of this etherification mixture is passed into a secondary reaction.

Examples which may be mentioned of a hydrocarbon mixture containing i-butene are a C$_4$-cut as obtained on thermal cracking after the removal of butadiene and, if present, of aromatics, and a C$_4$-cut from a catalytic cracking plant. The typical composition of such C$_4$-cuts is shown in the following Table:

TABLE 1

|  | C$_4$ from steam cracker | C$_4$ from cat cracker |
| --- | --- | --- |
| n-butane | 6–8% by weight | about 10% by weight |
| i-butane | 2–3% by weight | about 34% by weight |
| i-butene | 40–45% by weight | about 15% by weight |
| n-butene-1 | 24–28% by weight | about 13% by weight |
| n-butene-2 | 19–21% by weight | about 28% by weight |

Methanol is added to the i-butene-containing feed hydrocarbon mixture in essentially an equimolar amount, relative to the i-butene contained in the hydrocarbon mixture. Examples which may be mentioned of this are a molar ratio of methanol to i-butene of 0.9 to 1 to 1 to 0.9, preferably 0.95 to 1 to 1 to 0.95, particularly preferably about 1 to 1.

The etherification reaction is carried out in a known manner on an acid cation exchange material, for example on a styrene/divinylbenzene polymer containing sulphonic acid groups, in a solid or suspended layer at a temperature of 30° to 120° C., preferably 40° to 90° C., and under a pressure of 1 to 50 bar, preferably 3 to 20 bar, with a weight hourly space velocity (WHSV) of 0.1 to 15 kg of total feed materials per kilogram of cation exchange material per hour. In this reaction, the pressures and temperatures mentioned are so adjusted relative to one another that the etherification reaction proceeds in liquid phase.

The etherification mixture leaving the etherification reactor can be subdivided, for example to improve the control of the reaction temperature, and one part stream is returned via a cooler and a circulation pump to the inlet of the etherification reactor and passes through the etherification reactor once more together with fresh feed material. The other part of the subdivided etherification mixture can then be passed to the working-up. However, in a further variant this second part of the subdivided etherification mixture can also be passed to a second etherification reactor and only after passing through this second etherification reactor passed to the working-up. This second process variant also contributes to increasing the conversion.

After passing through the entire etherification stage, according to the invention the etherification mixture is separated by distillation into its constituents and simultaneously a part of the etherification mixture is passed into a secondary reaction. To do this, the etherification mixture is fed into a distillation column. This column has, for example, 30 to 80, preferably 40 to 70, plates. It can be designed as a bubble cap column or as a sieve tray column or any other distillation column with trays or packing materials which provides sufficient separating performance. This distillation column is operated under a pressure of 1 to 10 bar, preferably 3 to 7 bar and particularly preferably 4 to 6 bar.

A liquid distillate stream is taken off above the feed stream of the etherification mixture to the distillation column. The amount of this distillate stream is about 50 to 200%, preferably 75 to 150%, of the amount of the hydrocarbon raffinate which is removed at the top of the distillation column and is substantially free of i-butene and of methanol. This distillate stream taken off is then passed to a reactor which is packed with an acid cation exchange material and which is designed, for example, as a fixed-bed reactor. The acid cation exchange material used can be the same as used in the etherification reaction described above. An example which may also be mentioned here is a styrene/divinylbenzene exchange material which contains sulphonic acid groups and is in the H+-form. However, any other strongly acid cation exchange material which is in the H+-form, for example based on phenol-formaldehyde, is also suitable and familiar to an expert. The distillate stream taken off can be passed over the catalyst at the same WHSV as mentioned above for the etherification reaction. A WHSV of 1 to 5 is preferably set.

At the inlet to this fixed-bed reactor the distillate stream taken off has a temperature of, for example, 30° to 100° C., preferably 40° to 70° C. After passing through this fixed-bed reactor the distillate stream taken off is returned to the process below its take-off point. This return into the process can be effected, for example by feeding-in into the starting materials methanol and C4-raffinate I before entry into the etherification reactor, by feeding-in before entry into a second etherification reactor or by feeding-in into the distillation column. The return into the distillation column can take place into the stripping zone or into the enriching zone up to below the take-off point of the distillate stream, for example, together with the feeding-in of the reaction mixture leaving the etherification reaction into the distillation column. This manner of return into the distillation column is preferable. The return into the enriching zone of the distillation column between the feed point of the reaction mixture and a point below the take-off point of the distillation stream for the secondary reactor is particularly preferable.

The fixed-bed reactor is operated under a pressure which, depending on the inlet temperature, is sufficient to maintain the distillate stream taken off in the liquid phase during its passage through this fixed-bed reactor.

Particularly preferably the distillate stream taken off is passed into the fixed-bed reactor at the temperature which prevails at the take-off point of the distillation column.

BRIEF DESCRIPTION OF DRAWING

The way the process according to the invention is generally carried out may be described by way of example by means of the attached FIGURE which is a flow diagram.

DESCRIPTION OF SPECIFIC EMBODIMENT

Referring to the drawing, the isobutene-containing C4-mixture (1) and an amount of methanol (2) which is approximately equivalent to the content of i-butene are introduced into the reactor (3). This reactor can be for example a fixed-bed reactor or a tube reactor.

The product stream of the reactor can be, for example, subdivided and one part recombined with the feed stream for the reactor (3), whilst the other part stream is passed into a second reactor (4) which, in general, is packed with the same catalyst as (3). The catalyst in the second reactor (4) can in general be designed as a fixed-bed catalyst. The liquid product of the second reactor (4) is fed into a distillation column (5). Above the inlet of the etherification mixture to the distillation column, a liquid distillate stream (6) is taken from the distillation column and passed through a secondary reactor (7), for example from the bottom to the top. The catalyst in this secondary reactor (7) can be, for example, the same catalyst as in the reactors (3) and (4) described above and can be designed, for example, as a fixed-bed. After leaving the secondary reactor (7) the distillate stream taken off is returned below its take-off point into the distillation column. A temperature control is generally not required. The top product of the distillation column (5) is condensed in a cooler and part of it, from a condensate divider (8), is returned as reflux at the top of the column. The substantially i-butene-free top product (9) is taken from the condensate divider (8). The reflux ratio (reflux/ take-off=R/T) is generally set at a value of 0.1 to 5, preferably 0.5 to 2. One part of the bottom product of the column is recirculated via the heater (10) and the other part is taken off as pure MTBE (11).

The invention also relates to a device for the simultaneous distillative working-up and secondary reaction of etherification mixtures containing methyl tert.-butyl ether (MTBE), i-butene and methanol, which device comprises a distillation column which has the following features:

(a) a feed line for the etherification mixture,
(b) at the bottom a reboiler which is in itself known and a take-off device for the MTBE,
(c) at the top a condensate divider which is in itself known for the reflux and take-off of the residual C4-mixture which is free of MTBE and substantially free of i-butene and methanol.
(d) a take-off line for a distillate stream above the feed point of the etherification mixture into the column and
(e) a reactor which is packed with an acid cation exchange material and into which the distillate stream taken off is passed.

The return of the mixture leaving the reactor for the secondary reaction into the etherification reactor, if desired into a second etherification reactor or into the distillation column, can be effected in the form described above. The device according to the invention therefore preferably also has a feed point for the mixture leaving the secondary reactor. In a particularly preferable form, this feed point is in the enriching zone of the distillation column between the feed point of the etherification mixture and a point below the take-off point for the distillate stream.

With the aid of the process according to the invention it is possible to obtain in the distillation column (5) which is acting as a debutanizer a top stream which has an i-butene content of below 0.6% by weight, frequently of below 0.4% by weight, and a methanol content of below 0.8% by weight, frequently below 0.6% by weight. A C$_4$-raffinate II of this type, owing to the given low amounts of i-butene and methanol admixed, is suitable, in general without further treatment, for further processing, for example for the preparation of maleic anhydride, methyl ethyl ketone, pure butene-1 and of the dimers and oligomers of n-butene.

Only in a few cases will it be necessary to remove also the small residual content of methanol mentioned; for example, this is advantageously done when isolating butene-1. The bottom product in the process according to the invention is MTBE which is substantially free of methanol and can be directly passed onto a further use, for example as a fuel additive or solvent.

In contrast to processes of the state of the art which to obtain substantially complete coversion of the i-butene require large methanol excesses and correspondingly long residence times in the reaction zone or require a multistage separation of the C$_4$-fraction into its constituents with a correspondingly high consumption of energy, the process according to the invention permits shorter residence times, a lower consumption of energy, lower investment costs and makes possible a substantially complete conversion of methanol and of i-butene without using more expensive process steps. An example which may be mentioned of the i-butene conversion is a conversion of over 99% by weight.

EXAMPLE 1

500 ml (=300 g) of a C$_4$-mixture containing 41% by weight of i-butene (=2.20 mols) are passed per hour, after mixing with 90 ml (=71.9 g=2.22 mols) of methanol per hour and pre-heating to 50° C., into a fixed-bed reactor which is 0.75 meters long and has an internal diameter of 2.5 cm and is packed with 0.36 l of an acid cation exchange material which is based on a styrene/divinylbenzene resin which contains sulphonic acid groups, is in a macroporous form and has an ion exchange capacity of 1.4 mol/l. A part of the reaction product of this reactor is recycled and cooled, via a cooler, down to the reactor inlet temperature. The reactor is insulated and operates as an adiabatic reactor. The reactor outlet temperature is 77° C. The ratio of fresh C$_4$-mixture to circulation mixture is 1 to 2. The non-returned reaction mixture of the first reactor, after cooling down to 50° C., passes into a second fixed-bed reactor which is packed with 0.75 l of the same catalyst as the first reactor and has a height of 1.6 meters and an internal diameter of 2.5 cm. The reaction product (etherification mixture) of this second reactor, after letting down to 5 bar, passes to a distillation column having 60 actual trays. The feed point is located at the 15th tray of the column. The column operates under a pressure of 5 bar. The top temperature of the column is 44° C. and the bottom temperature is 107° C.

250 ml of liquid per hour are taken off at the 45th tray of the column and passed, via a pump, at the bottom into a secondary reactor which is located in the sidestream and has a height of 0.3 m and a diameter of 2.5 cm. It is packed with the acid cation exchange material described above. The inlet temperature depends on the take-off point and is about 50° C. The mixture leaving the secondary reactor returns into the distillation column at the 30th tray.

At the inlet to the secondary reactor, the content of i-butene is 1.2% by weight and of methanol 1.0% by weight. At the outlet of the secondary reactor the i-butene content has decreased to 0.1% by weight and the methanol content to 0.3% by weight.

The C$_4$-raffinate II taken off at the top has the following composition:

| | |
|---|---|
| n-butane | 18.1% by weight |
| i-butane | 6.4% by weight |
| i-butene | 0.6% by weight |
| n-butene-1 | 43.9% by weight |
| trans-butene-2 | 18.3% by weight |
| cis-butene-2 | 11.9% by weight |
| and methanol | 0.8% by weight |

The bottom product taken off has the following composition:

| | |
|---|---|
| MTBE | 98.4% by weight |
| methanol | 0.3% by weight |
| C$_4$-hydrocarbons | 0.1% by weight |
| C$_8$-hydrocarbons | 0.9% by weight |
| H$_2$O | 0.2% by weight |
| and tert.-butanol | 0.1% by weight |

EXAMPLE 2

500 ml (=300 g) of a C$_4$-mixture containing 41% by weight of i-butene (=2.20 mols) are passed per hour, after mixing with 90 ml (=71.9 g=2.22 mols) of methanol per hour and pre-heating to 50° C., into a fixed-bed reactor which is 0.75 meters long and has an internal diameter of 2.5 cm and is packed with 0.36 l of an acid cation exchange material which is based on a styrene/divinylbenzene resin which contains sulphonic acid groups, is in a macroporous form and has an ion exchange capacity of 1.4 mol/l. A part of the reaction product of this reactor is recycled and cooled, via a cooler, down to the reactor inlet temperature. The reactor is isolated and operates as an adiabatic reactor. The reactor outlet temperature is 77° C. The ratio of fresh C$_4$-mixture to circulation mixture is 1 to 2. The non-returned reaction mixture of the first reactor, after cooling down to 50° C., passes into a second fixed-bed reactor which is packed with 0.75 l of the same catalyst as the first reactor and has a height of 1.6 meters and an internal diameter of 2.5 cm. The reaction product (etherification mixture) of this second reactor, after letting down to 5 bar, passes to a distillation column having 60 actual trays. The feed point is located at the 15th tray of the column. The column operates under a pressure of 5 bar. The top temperature of the column is 44° C. and the bottom temperature is 107° C. The top stream of the column is liquefied in a condenser and the condensate is passed into a condensate divider. 250 ml are taken as top product from the condensate divider and 500 ml are passed as reflux, via a pump, at the bottom into a secondary reactor. The secondary reactor located in the reflux has a height of 0.3 m and a diameter of 2.5 cm. It is packed with the acid cation exchange material described above. The temperature in the reactor is about 45° C. The mixture leaving the secondary reactor is returned at the uppermost tray into the distillation column.

At the inlet of the secondary reactor the content of i-butene is 0.4% by weight and the methanol content 0.6% by weight. At the outlet of the secondary reactor the i-butene content has descresed 0.1% by weight and the methanol content to 0.4% by weight.

The C₄-raffinate II taken off at the top has the following composition:

| | | |
|---|---|---|
| n-butane | 18.0% | by weight |
| i-butane | 6.4% | by weight |
| i-butene | 0.4% | by weight |
| n-butene | 44.1% | by weight |
| trans-butene-2 | 18.5% | by weight |
| cis-butene-2 | 12.0% | by weight |
| and methanol | 0.6% | by weight |

No MTBE could be detected in the top product.

The bottom product taken off has the following composition:

| | | |
|---|---|---|
| MTBE | 98.8% | by weight |
| methanol | <0.2% | by weight |
| C₄-hydrocarbons | <0.1% | by weight |
| C₈-hydrocarbons | 0.9% | by weight |
| H₂O | <0.2% | by weight |
| and tert.-butanol | <0.1% | by weight |

What is claimed is:

1. A process for the production of methyl tert.-butyl ether and of a hydrocarbon raffinate which is substantially free of isobutene and of methanol from methanol and a hydrocarbon mixture containing isobutene, which consists essentially of contacting methanol and isobutene contained in a hydrocarbon mixture in substantially equimolar amounts in a reaction zone in the presence of an acid cation exchange material, feeding the resultant reaction mixture into a distillation column, distilling off an overhead, withdrawing of bottoms and simultaneously with distilling off said overhead and withdrawing said bottoms, removing a side cut from said distillation column, passing said side cut into a secondary reaction zone containing an acid cation exchange material and reacting components therein to form additional methyl tert.-butyl ether, feeding the reaction product of said secondary reaction zone back into said distillation column at a point below the point at which said side cut is withdrawn, recovering a bottoms product which is substantially pure methyl tert.-butyl ether and obtaining an overhead containing hydrocarbons and unreacted methanol.

2. A process according to claim 1 wherein the side cut of the reaction mixture fed to a secondary reaction zone is withdrawn from the distillation column at a point above the feed inlet point of the reaction mixture to said distillation column and, after it has passed through said second reaction zone, is returned to said distillation column.

3. A process according to claim 1 wherein the side cut of the reaction mixture withdrawn from the distillation column and passed into a secondary reaction zone is a liquid distillate and is passed to said secondary reaction zone in liquid phase.

4. A process according to claim 1 wherein the secondary reaction in the secondary reaction zone is carried out at a temperature of 30° to 110° C.

5. A process according to claim 4 wherein the secondary reaction zone is maintained at a temperature of 40° to 70° C.

6. A process according to claim 1 wherein the secondary reaction is carried out at the temperature which prevails at the point at which the components are taken from the distillation column for passage to the secondary reaction zone.

7. A process according to claim 1 wherein the distillation column is operated at a ratio of reflux to take-off (R/T) of 0.1 to 5.

8. A process according to claim 2 wherein the reaction mixture which has passed through said secondary reaction zone is returned to said distillation column at a point below the point at which said side cut is withdrawn.

9. A process according to claim 1 wherein a portion of the bottoms are reboiled and returned to the reaction mixture and bottoms substantially free of isobutene and hydrocarbon and rich in methyl tert.-butyl ether are obtained.

* * * * *